United States Patent [19]
Chang et al.

[11] Patent Number: 5,400,602
[45] Date of Patent: Mar. 28, 1995

[54] CRYOGENIC TRANSPORT HOSE

[75] Inventors: ZhaoHua Chang, Poolesville, Md.; John Baust; Larry Pottorff, both of Candor, N.Y.

[73] Assignee: Cryomedical Sciences, Inc., Rockville, Md.

[21] Appl. No.: 87,289

[22] Filed: Jul. 8, 1993

[51] Int. Cl.$^6$ .......................... F17C 13/00
[52] U.S. Cl. ........................ 62/50.7; 62/293; 128/DIG. 27; 138/111; 138/149; 606/20
[58] Field of Search .............. 62/50.1, 50.7, 293; 128/DIG. 27; 138/111, 118.1, 149; 606/20, 23, 24

[56] References Cited

U.S. PATENT DOCUMENTS

| | | | |
|---|---|---|---|
| 2,969,092 | 1/1961 | Johnson | 62/50.7 |
| 3,266,492 | 8/1966 | Steinberg | 606/23 |
| 3,269,422 | 8/1966 | Matthews et al. | 138/149 |
| 3,397,720 | 8/1968 | Jones | 62/50.1 |
| 3,421,508 | 1/1969 | Nestrock | 606/23 |
| 3,782,386 | 1/1974 | Bareer et al. | 62/293 |
| 3,907,339 | 9/1975 | Stumpf et al. | 606/20 |
| 3,971,383 | 7/1976 | van Gerven | 62/293 |
| 4,015,606 | 4/1977 | Mitchiner et al. | 62/293 |
| 4,194,536 | 3/1980 | Stine et al. | 138/111 |
| 4,380,253 | 4/1983 | Mead et al. | 138/149 |
| 4,726,194 | 2/1988 | Mackay et al. | 62/50.7 |
| 4,924,679 | 5/1990 | Brigham et al. | 138/149 |
| 5,072,591 | 12/1991 | Grange et al. | 62/50.7 |

FOREIGN PATENT DOCUMENTS 0437377 7/1991 European Pat. Off. ............ 606/24

OTHER PUBLICATIONS

F. W. Forbes et al., "Expandable Cryogenic Pipe", (1963) Advances in Cryogenic Engineering, vol. 8, Plenum Press, New York, pp. 411–417.

R. B. Scott, "Transfer of Liquefied Gases", Cryogenic Engineering, Chapter VIII, pp. 249–267.

*Primary Examiner*—Ronald C. Capossella

[57] ABSTRACT

A hose designed to facilitate supply and return of cryogenic fluid such as a liquefied gas includes supply and return conduits wrapped in multiple layers of reflective metallized material, which is surrounded by a layer of foam material which is, in turn, surrounded by a protective outer layer such as, for example, a woven cover. The conduits are made of a material such as polytetrafluoroethylene. The inventive hose is lightweight and maintains flexibility for extended periods of time with cryogenic fluid flowing through the conduits.

11 Claims, 1 Drawing Sheet

CRYOGENIC TRANSPORT HOSE

BACKGROUND OF THE INVENTION

The present invention relates to a cryogenic transport hose. More particularly, the invention relates to a lightweight, flexible hose capable of transporting cryogenic fluids, especially cryogenic liquids, especially for use in connection with cryosurgical procedures.

In the prior art, the hoses have been developed for the purpose of supporting the movement of cryogenic fluids. However, effectiveness of such hoses has been limited since it has been difficult to design such a hose with sufficient insulative properties to limit heat gain of the liquid cryogen over any significant distance. In fact, the development of the field of cryosurgery has been limited in part by the inability to transport a boiling liquid any significant distance without gasification.

In designing a cryogenic transport hose, the following characteristics must be incorporated:

(1) Low thermal conductance: the hose must be provided with sufficient insulative properties to limit the degree of temperature gain of the cryogenic fluid per unit length;

(2) High degree of flexibility: the materials from which the hose is constructed must maintain flexibility even at temperatures below $-100°$ C.;

(3) Reliability: the hose must be constructed in such a manner that it will not leak and will not fail even though subjected to numerous cycles of cooling and subsequent warming; this is especially important in the intended application in connection with cryosurgical probes;

(4) Soft, pliable outer covering: the hose must have an outer covering which is not abrasive when handled by the user but which provides adequate protection against rough handling, is easily applied and provides an attractive appearance;

(5) Tolerance to twisting and lateral deformation: as pointed out in (2) above, the materials from which the hose is constructed must be sufficiently flexible to prevent failure regardless of the contortions to which the hose is subjected. The ability to be twisted, flexed, etc. also allows the hose to be folded, or looped into a small compact configuration for storage and shipping.

Additionally, given the state of the art concerning cryosurgical instruments, the hose must be provided with a fluid connector allowing secure, reproducible and quick connection to a source of cryogenic fluid. Furthermore, the hose must be provided with a coupling at its distal end allowing coupling of the hose to various types of cryogenic surgical probes. Additionally, it would be advantageous to provide such a hose with means facilitating monitoring of the temperature of the cryogenic fluid at the hose/probe coupling and/or the temperature of or at the probe tip.

It is with these aspects in mind that the present invention was developed.

The following prior art is known to Applicants:

U.S. Pat. No. 3,269,422 to Matthews et al. discloses a composite tubing product and apparatus and method. In the embodiments of Matthews et al., metallic tubes are surrounded by a layer of filler material which in some embodiments, is surrounded by a wrapping "such as for instance a laminated Dacron-asbestos tape known as Mylar and having good heat insulating characteristics." The present invention differs from the teachings of Matthews et al. as contemplating the use of flexible, plastic conduits directly surrounded by an insulative wrapping.

U.S. Pat. No. 4,194,536 to Stine et al. discloses a composite tubing product including two inner tubes in heat transfer relationship surrounded by a flexible thermal barrier of multiple layers of low bulk, low density fibrous glass. A filler of fibrous or foam material is present between the tubes and the barrier layer and a binder member, which may comprise metallic film, may be wrapped around the tubes to secure a heating line spirally wrapped around the tubes. Of course, in the present invention, the intent is to maintain cryogenic fluid within two conduits as cool as possible. Thus, the teachings of Stine et al. appear to be at cross-purposes with the teachings of the present invention.

U.S. Pat. No. 4,380,253 to Mead et al. discloses a heat-insulated hose for liquified gases which includes an inner hose resistant to cyrogenic temperatures and a plurality of successive layers of heat insulating material. In the preferred embodiment, Mead et al. contemplates the insulating layers as comprising a plurality of layers of polystyrene foam with intervening layers of Mylar film. The Mylar film of Mead et al. is not disclosed as metallized. The present invention differs from the teachings of Mead et al. as contemplating surrounding two cryogenic fluid conveying conduits directly with a plurality of layers of metallized reflective foil and surrounding the layers of foil with foam.

U.S. Pat. No. 4,924,679 to Brigham et al. discloses apparatus and method for evacuating an insulated cryogenic hose. As disclosed by Brigham et al., vacuum insulation is provided as an insulative layer. Also disclosed is the use of a wrinkled reflectorized foil sheet surrounding the cryogenic conduit. As a modification, Brigham et al. illustrate, but do not discuss, use of a urethane foam insulation layer. The present invention differs from the teachings of Brigham et al. as contemplating a cryogenic transport hose wherein supply and return conduits are directly surrounded by a plurality of layers of reflective metallized foil material surrounded by a foam insulative layer. The present invention is advantageous as compared to the teachings of Brigham et al. since vacuum insulation layers have proven unreliable in cryogenic transport hoses since the twisting and lateral deformation of such hoses, in use, along with multiple cooling/warming cycles, often cause the vacuum layer to fail.

U.S. Pat. No. 5,072,591 to Grange et al. discloses a flexible transfer line exhaust gas shield. In Grange et al., a flexible transfer line is supported within a plastic tube around which is wrapped a shield of flexible metal braid or tape surrounded by a super-insulation layer. The present invention differs from the teachings of Grange et al. as contemplating a hose containing supply and return conduits made of flexible plastic, surrounded by multiple layers of metallized reflective foil and surrounded by a foam insulation layer.

SUMMARY OF THE INVENTION

The present invention relates to a cryogenic transport hose. The present invention includes the following interrelated objects, aspects and features:

(A) In a first aspect, the inventive hose includes two flexible conduits, one of which is provided to supply cryogenic fluid from a proximal end of the hose to a distal end thereof. The other conduit is provided to facilitate return of cryogenic fluid from the distal end of the hose back to the proximal end of the hose and thence back to a reservoir. The conduits are preferably made of flexible plastic material such as, for example, polytetrafluoroethylene.

(B) The proximal and distal ends of the hose are provided with fluid couplings. At the proximal end, the fluid coupling includes two separate coupling members connected to cryogenic fluid supply and return lines, respectively. At the distal end, the coupling member allows coupling of the supply and return conduits to corresponding supply and return conduits of a cryosurgical probe.

(C) The supply and return conduits are surrounded by a plurality of wrapped layers of insulative tape which, in the preferred embodiment of the present invention, comprises metallized reflective plastic foil, such as polyethylene terephthalate, commercially available as Mylar, or other similar reflective flexible foil film. In the preferred embodiment of the present invention, the Mylar foil wrapping is provided in from 2 to 30 layers. Furthermore, the metallization of the Mylar wrapping may be, and preferably comprises aluminization.

(D) In surrounding relation to the layers of metallized Mylar foil wrapping, a self-sealing foam insulation is provided. In the preferred embodiment, the insulation is pre-slit so that it may be mounted about the wrapped conduits and the faces of the slit may be glued for longitudinal seaming. In the preferred embodiment, the foam insulation is made of closed cell polyolefin foam.

(E) Surrounding the foam insulation is an external cover made of an appropriate lightweight material. The external cover provides protection against rough handling as well as providing an attractive appearance. The external cover may be made of any suitable plastic material. In the preferred embodiment of the present invention, the cover is made of braided sleeving which is known for its lightweight flexible and expandable characteristics. The expandability of the preferred cover material facilitates the assembly process as described.

(F) A thermocouple may be provided within the hose, contained within the "chamber" formed by the layers of metallized Mylar foil wrapping, within which "chamber" is also contained the flexible plastic cryogenic fluid conduits. The thermocouple is located at the distal end within the cryosurgical probe coupling and the thermocouple wire is electrically connected between the thermocouple and an appropriate temperature indicator and extends within the "chamber" from the distal end of the hose to the proximal end thereof, terminating at an electrical connector adjacent the proximal coupling.

As such, it is a first object of the present invention to provide a cryogenic transport hose.

It is a further object of the present invention to provide such a cryogenic transport hose including two flexible conduits contained within several layers of an insulative wrap.

It is a still further object of the present invention to provide such a hose with foam insulation surrounding the several layers of insulative wrap.

It is a yet further object of the present invention to provide such a hose with suitable coupling members at the proximal and distal ends thereof.

It is a yet further object of the present invention to provide such a hose with a thermocouple designed to sense cryogenic fluid temperature at the distal coupling and/or to allow measurement of the temperature of the probe tip.

These and other objects, aspects and features of the present invention will be better understood from the following detailed description of the preferred embodiment when read in conjunction with appended drawing figures.

SPECIFIC DESCRIPTION OF THE PREFERRED EMBODIMENT

Figure 2:
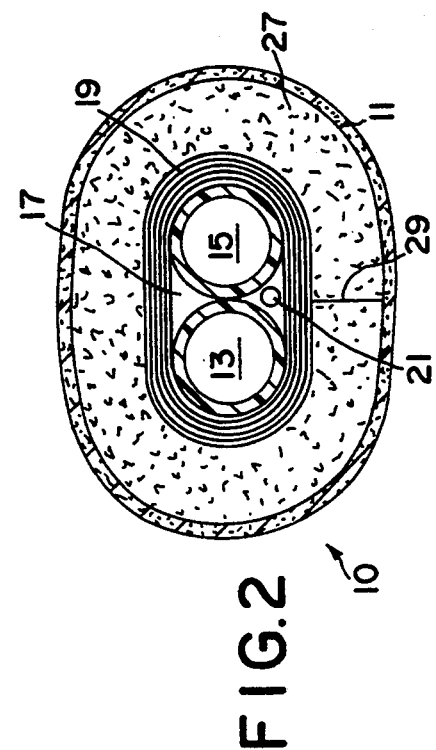
FIG. 2 shows an enlarged cross-sectional view along the line II—II of FIG. 1.

With reference to the figures, the inventive hose is generally designated by the reference numeral 10 and is seen to include an outer covering 11 preferably made of a flexible, expandable plastic (e.g. polypropylene) material such as, for example, braided sleeving, as shown. The cover material, being an exposed outer surface, should also be sterilizable. A particularly suitable braided sleeving is available from Bentley Harris under the Expando ® trademark of protective oversleeving products. This product is available, for example, as a tight weave, ⅜ inch expandable mesh sleeve with tulip (self-flaring) construction to facilitate insertion of the foam tubing.

Within the hose 10, a flexible supply conduit 13 and a flexible return conduit 15 are provided. The conduits 13 and 15 are preferably made of low temperature resistant and insulative material, especially fluorocarbon polymer, such as polytetrafluoroethylene, or other fluoroethylene polymer such as tetrafluoroethylene-hexafluoro-propylene copolymer (FEP), which are available under the registered "TEFLON" trademarks owned by E. I. dupont. Tubing made from Teflon ® FEP grade 140 having a tensile strength (ASTM D 1706) of 4000 psi has been successfully used in this invention. This material is chosen for the conduits 13 and 15 because it maintains flexibility and seal integrity within the range of temperatures contemplated herein, namely from below −100° C. (e.g. as low as −210° C.) to room temperature. It is convenient that conduits 13 and 15 are formed from different color tubing to facilitate assembly of the coupling connections to their respective supply and return lines. For example, FEP Teflon ® 140 tubing is available in natural (white) and blue tinted colors.

As best seen in FIG. 2, the conduits 13 and 15 are arranged in parallel and are located adjacent one another and are contained within a "chamber" 17 formed by a multiplicity of wrapped layers of flexible, reflective, foil insulative material designated by reference numeral 19. In the preferred embodiment of the present invention, the metallized reflective foil is formed from polyethylene terephthalate film, commercially available under the trademark MYLAR. One such product which has been successfully used in the present invention is the pre-wrinkled single side aluminized polyester film (0.00025 inch) available from Metallized Products, Inc. of Winchester, Mass., under the trademark NRC-2 ®. However, other metallizable thin foil films, such as polyolefins, polycarbonates, other polyesters, and the like, may also be used. Generally, anywhere from 2 to 30, preferably 6 to 30, wrapping layers are used to provide the requisite degree of insulation while still maintaining flexibility. The metallization of the foil 19, may be on one or both surfaces, and in the preferred embodiment, comprises aluminization since aluminum is extremely lightweight and may be provided with a reflective finish. The "chamber" 17 is not evacuated. Rather, the conduits 13 and 15 are placed adjacent one another and the layers of metallized foil wrapping 19 are wrapped therearound.

MYLAR type polyester is chosen as the preferred material for use as the wrapping 19 because this particular material acts as a radiation shield as well as a vapor barrier to prevent the intrusion of moisture or atmospheric gases were the outer seal to be compromised in any way such as, for example, due to degradation of the foam. Additionally, MYLAR is an extremely strong material even at the thicknesses employed and provides significant structural strength to the hose 10.

It is also preferred that the foil wrapping layers are wrinkled, roughened, or similarly deformed to minimize surface to surface contact between adjacent layers and, thereby, further enhance the insulative characteristics. Pre-wrinkled metallized Mylar is commercially available, such as the NRC-2 ® mentioned above.

Figure 1:
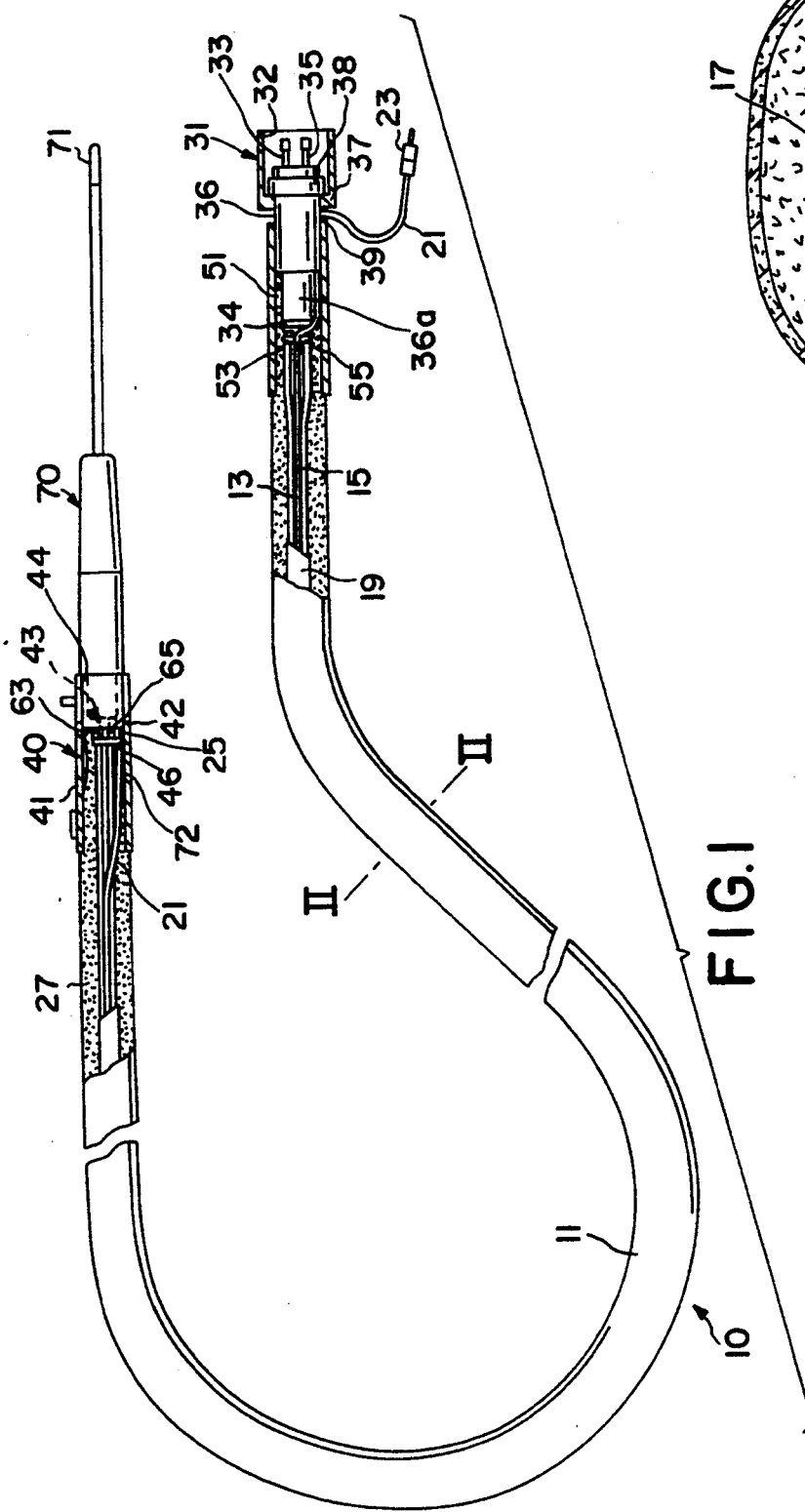
FIG. 1 shows a side view of the inventive hose, with portions broken away to show detail and with other portions shown in cross-section.

Also contained within the "chamber" 17 is a thermocouple wire 21 which provides electrical connection between an electrical thermocouple connector 23 (FIG. 1) and an optional thermocouple 25 (FIG. 1). The male connector 23 couples the thermocouple wire 21 to a temperature indicator (not shown) designed, as is well known to those skilled in the art, to receive electrical signals from the thermocouple 25 and convert them into indications of temperature. An FEP Teflon jacketed and insulated, unshielded thermocouple extension wire (2 parallel conductors) is available from Belden, a division of Cooper Industries, as grade TX 83934, and has been conveniently used as thermocouple wire 21. The significance of the location of the thermocouple 25 will be described in greater detail hereinafter.

Surrounding the insulative wrapping layers 19 is a relatively thick layer of foam insulation designated by the reference numeral 27. In the preferred embodiment, the foam layer 27 is preformed to the appropriate shape and includes a longitudinal seam 29 (FIG. 2) having abutting faces which may be sealed together through the use of an appropriate adhesive. The braided outer covering 11 surrounds foam layer 27.

In the preferred embodiment of the present invention, the insulating foam which is employed for foam layer 27 comprises a closed cell polyolefin foam, e.g. polyethylene foam. This material is chosen due to its comparative low density, relatively higher strength to weight ratio than other foam insulation materials, tolerance of the severe thermal and mechanical stresses which are imposed thereon by multiple cooling/warming cycles between ambient temperature and below $-100°$ C. and tolerance of heat up to $100°$ C. Furthermore, the closed cell polyolefin insulation also comprises a self-functioning vapor barrier. For a nominal one-inch diameter hose, polyethylene foam tubing with $\frac{3}{8}$ inch ID and $\frac{3}{8}$ inch wall thickness may be used. A suitable self-sealing semi-slit expanded, closed-cell polyethylene foam pipe insulation is commercially available in, for example, $\frac{3}{8}$ inch, $\frac{1}{2}$ inch and $\frac{3}{4}$ inch thickness with inside diameters (ID) ranging from $\frac{3}{8}$ inch to $2\frac{1}{8}$ inch, e.g. product no. 4734K22, from McMaster-Carr, or Imcoa under the Imcolock ® trademark.

At the proximal end of hose 10, an internally threaded female coupling nut 31 is provided to securingly engage fluid coupling tube 33 for the conduit 13 and fluid coupling tube 35 for the fluid conduit 15 to corresponding couplings/tubing leading to an external supply of cryogenic fluid, e.g. liquid nitrogen, and to a collection reservoir or to atmosphere for the used/return cryogenic fluid, which corresponding couplings will be housed within an external (male) coupling to threadingly engage with the threads 32 of coupling nut 31. The fluid coupling 33 is thereby fluid tightly connected to tubing (not shown) which conveys cryogenic fluid from a source thereof. The fluid coupling 35 is similarly fluid tightly connected via appropriate tubing (not shown) to a reservoir (not shown) where spent cryogenic fluid and gas resulting from heating of the cryogenic fluid are stored for re-use. Alternatively, the returning cryogen may, if desired, be vented to atmosphere.

The coupling nut 31 includes enlarged end portion 37 designed to overlie hose connector structure 36 and tightly engage with enlarged portion 38 of structure 36 when coupling nut 31 is threadingly engaged with the external coupling. The fluid coupling tubes 33, 35 are extended completely through and beyond end 34 of the reduced diameter section 36a of structure 36. The extending portions of tubes 33, 35 are fluid tightly fitted within and interconnected to the proximal ends of conduits 13 and 15, respectively, and secured thereto by clamp fittings 53 and 55, respectively.

As shown in FIG. 1, the enlarged proximal end 37 of coupling 31 is spaced from protective sleeve 39 to provide an opening to thermocouple wire 21 to extend beyond hose 10 so that connector 23 may be easily engaged to an appropriate female thermocouple connector. Sleeve 39 overlies and further secures the fitting between the proximal end of the hose and the hose connector structure 36. As also shown in FIG. 1 hose connector structure 36 is fitted within the proximal end of foam insulation 27 such that foam insulation overlies and tightly engages the intermediate diameter portion 36a. Furthermore, a hose clamp 51 may be used to further secure the foam insulation to section 36a as well as to secure thermocouple wire 21 to section 36a. Preferably, hose clamp 51 is covered by a strip of adhesive tape, e.g. Teflon tape, to avoid exposure of the clamp.

As also shown in FIG. 1, the distal coupling or probe end connector sleeve, generally designated by the reference numeral 40, interconnects the distal end of the hose 11 to the proximal end of a cryosurgical probe 70 which is schematically shown and includes a probe end (tip) 71. The cryosurgical probe 70 may be of any suitable type provided it includes provision, including internal flow passages, to facilitate receipt and return of cryogenic fluid from and to, respectively, the conduits 13 and 15. A preferred cryosurgical probe is that described in the commonly assigned copending U.S. patent application Ser. No. 07/756,287, filed Sep. 6, 1991, incorporated herein by reference thereto. In fact, in an especially preferred embodiment, the cryogenic transport hose and the cryosurgical probe are preassembled and ready for use after coupling at the proximal end to the cryogen refrigerant supply/return.

Distal coupling 40, as shown in FIG. 1, includes a protective sleeve 41 which overlies cover 11 of hose 10 and the proximal portion of probe 70. Sleeve 41 includes a slightly tapered exterior portion 42 and a corresponding slightly flared interior portion 44 terminating at an interior step 46 approximately midway along the length of sleeve 41. The flared interior and step provide easy access and a stop member for the proximal end of probe 70. As generally known in the art, the distal ends of conduits 13, 15 are coupled via coupling connectors 63, 65 to inlet (supply) and outlet (return) tubes, respectively, extending from the proximal end of cryosurgical probe 70. Underlying protective sleeve 41, foam insulation 27 defines an internal chamber 43 in which a thermocouple 25 may be located so that the temperature of cryogenic fluid as it enters the cryosurgical probe may be monitored. However, more typically, although not part of the present invention, per se, it is generally more convenient to provide a thermocouple at probe tip 71 so that the temperature of the probe tip may be directly monitored. In this case, an appropriate thermocouple connector at the end of the probe is provided for quick connection to the thermocouple wire 21, such as at the portion 25. As described above in connection with the proximal end of hose 10 the foam insulation and wire 21 at the distal end connected to probe 70 may be secured with a hose clamp 72 which in turn may be secured by Teflon tape.

With the inventive hose 10 having been described in detail, its preferred mode of operation will now be explained.

The proximal coupling 31 is interconnected with a female coupling (not shown) which fluid tightly connects the conduits 13 and 15 to supply and return lines, respectively, for cryogenic fluid. The connector 23 may be connected to a suitable temperature indicator. The distal coupling 40 is coupled to cryosurgical probe 70.

Cryogenic fluid from a suitable source (not shown) is supplied via the fluid coupling 33 through the fluid conduit 13 to the distal coupling 40 where the cryogenic fluid is supplied to the interior of the cryosurgical probe 70. Cryogenic fluid is circulated within the cryosurgical probe 70 and is conveyed back to the coupling 40 where return cryogenic fluid enters the conduit 15 and returns through the hose 10 to the fluid coupling 35 and thence through the fluid line (not shown) to a reservoir where cryogenic fluid and any gas resulting from heating of cryogenic fluid may be stored for re-use. As cryogenic fluid is flowing through conduits 13 and 15, thermocouple 25 sends electrical signals corresponding to the temperature of the cryogenic fluid within chamber 43 via thermocouple wire 21 to electrical connector 23 and thence to a temperature indicator (not shown) so that the temperature of the cryogenic fluid as it enters cyrosurgical probe 70 may be continuously monitored and displayed. Similarly, when a thermocouple is provided at probe tip 71 electrical signals may be returned via additional thermocouple wires (not shown) to continuously monitor and display the probe tip temperature.

Applicants have found the inventive hose as described hereinabove to be quite advantageous as compared to prior art hoses. Hoses including a vacuum insulation chamber have performance which seriously degrades over time since the vacuum chamber is often compromised. In the wide range of temperatures in which the hose operates, slight cracks in the insulative layers of a vacuum insulated hose may occur resulting in loss of vacuum. The delicacy of vacuum insulation requires such hoses to be stored and handled extremely cautiously to prevent or, at least, delay vacuum leakage. With the present invention, which is not dependent on vacuum insulation, no such problems exist.

Total fabrication cost for a hose made in accordance with the teachings of the present invention, including labor and materials, represent only a small fraction of the total cost of a hose made including vacuum insulation. The difference in cost may be as much as a factor of 30. In fact, by virtue of low manufacturing costs, the hose of this invention can be, and preferably is, intended to be disposable after only a single or only a few uses. By disposing of the hose after only a single use, there will be no necessity for re-sterilization of the hose and couplings following use in a cryosurgical operation.

In the preferred embodiment of the present invention the entire overall diameter of the hose may be about one inch or less and the flexibility of the hose permits it to be folded in an extremely small area.

In a further important aspect, when liquid nitrogen at e.g. $-160°$ C. to $-209°$ C. or $-210°$ C. (e.g. sub-cooled liquid nitrogen) is used as the cryogenic fluid refrigerant, and the liquid nitrogen is initially admitted into the hose at ambient temperature, a portion of the liquid nitrogen inevitably vaporizes before the line is cooled enough to allow steady liquid flow. The duration of this transient cool-down time can be a critical consideration especially when the gas generated during this process cannot be adequately vented from the system. For a vacuum insulated hose, the cool-down time is much greater than that of the present invention, because, in a vacuum insulated hose, a much higher heat capacity exists due to the inherent metal configuration thereof. Consequently, the overall thermal performance of the present invention may be better than that of a vacuum hose, in many situations.

The cryogenic liquid transport hose of this invention offers many advantages in addition to its low cost, flexibility and light weight. It is a very efficient heat insulator, even at temperatures as low as $-210°$ C. and can remain flexible at the temperature of liquid nitrogen for as long as about 30 minutes or more. As such it is highly reliable and can be used for extended periods without leaking or cracking. Still another advantage of the cryogenic fluid (e.g. liquid nitrogen) transport hose of this invention is its ability to handle high as well as low rates of flow of the cryogenic fluid. For example, whereas the aforementioned transport hose contemplated in U.S. Pat. No. 5,072,591 to Grange, et al. is designed primarily for transporting liquid helium at a low flow rate, e.g. less than 2 liters per hour, the inventive hose is capable of handling either low flow rates or high flow rates, e.g. more than 60 liters per hour, as well as flow rates therebetween. High flow rates of, for example, 100 liters per hour, with the concommitant high pressures necessitated by such flow rates, can be safely accommodated by the transport hose of this invention.

As such, an invention has been disclosed in terms of a preferred embodiment thereof which fulfills each and every one of the objects of the present invention as set forth hereinabove and provides a new and useful cryogenic transport hose.

Of course, various changes, modifications and alterations in the teachings of the present invention may be contemplated by those skilled in the art without departing from the intended spirit and scope thereof. As such, it is intended that the present invention only be limited by the terms of the appended claims.

What is claimed is:

1. A cryogenic fluid transport hose, comprising:

a) a supply conduit and a return conduit, said conduits being made of a material which remains flexible and pliable at temperatures below −100° C.;

b) said conduits being wrapped within a plurality of layers of reflective wrapping defining a first vapor barrier;

c) said wrapping being surrounded by a lightweight foamed polymer insulative layer defining a second vapor barrier;

d) a flexible cover covering said lightweight foamed polymer insulative layer;

e) said hose having a proximal end and a distal end, said proximal end carrying a coupling adapted to be coupled to a source of cryogenic fluid for supplying cryogenic fluid to said supply conduit and for receiving cryogenic fluid from said return conduit, said distal end being adapted to be coupled to a cryosurgical probe.

2. The hose of claim 1, wherein said conduits are made of polytetrafluoroethylene.

3. The hose of claim 1, wherein said plurality of layers comprises from 2 to 30 layers of said reflective wrapping.

4. The hose of claim 3, wherein said reflective wrapping comprises aluminized polyethylene terephthalate foil.

5. The hose of claim 4, wherein said aluminized polyethylene terephthalate foil is wrinkled.

6. The hose of claim 1, wherein said lightweight foamed polymer insulative layer comprises closed cell polyolefin foam.

7. The hose of claim 1, wherein said lightweight foamed polymer insulative layer has a longitudinal split permitting assembly over said wrapping, said split having opposed faces bonded together, in assembly, over said wrapping.

8. The hose of claim 1, wherein said flexible cover is made of an expandable braided material.

9. The hose of claim 1, wherein said distal end includes a distal coupling adapted to couple to a cryosurgical probe.

10. The hose of claim 9, wherein said distal coupling includes a chamber containing temperatures sensing means.

11. The hose of claim 10, wherein said temperature sensing means comprises a thermocouple and an electrical conductor connected to said thermocouple and extending through said hose to said proximal end thereof.

* * * * *